US012718445B2

(12) United States Patent
Gong et al.

(10) Patent No.: US 12,718,445 B2
(45) Date of Patent: Aug. 25, 2026

(54) SPECT IMAGING PREDICTION MODEL CREATION METHOD AND APPARATUS, AND DEVICE AND STORAGE MEDIUM

(71) Applicant: Shanghai Radiodynamic Healthcare Technology, Shanghai (CN)

(72) Inventors: Nanjie Gong, Shanghai (CN); Boyang Pan, Shanghai (CN)

(73) Assignee: SHANGHAI RADIODYNAMIC HEALTHCARE TECHNOLOGY, Shanghai (CN)

(*) Notice: Subject to any disclaimer, the term of this patent is extended or adjusted under 35 U.S.C. 154(b) by 389 days.

(21) Appl. No.: 18/551,876

(22) PCT Filed: Mar. 26, 2021

(86) PCT No.: PCT/CN2021/083206
§ 371 (c)(1),
(2) Date: Sep. 22, 2023

(87) PCT Pub. No.: WO2021/139835
PCT Pub. Date: Jul. 15, 2021

(65) Prior Publication Data

US 2024/0177377 A1 May 30, 2024

(30) Foreign Application Priority Data

Mar. 24, 2021 (CN) ........................ 202110311613.7

(51) Int. Cl.
*G06T 12/00* (2026.01)
*A61B 6/00* (2006.01)
(Continued)

(52) U.S. Cl.
CPC .............. *G06T 12/20* (2026.01); *A61B 6/037* (2013.01); *A61B 6/5235* (2013.01);
(Continued)

(58) Field of Classification Search
CPC ............... G06T 11/006; G06T 2210/41; G06T 2211/421; G06T 2211/441; G06T 11/00;
(Continued)

(56) References Cited

U.S. PATENT DOCUMENTS

2013/0322717 A1* 12/2013 Bar-Shalev ............... G06T 7/74 382/131
2021/0205484 A1* 7/2021 Jin ....................... A61K 51/088
2023/0230297 A1* 7/2023 Goedicke .............. G06T 11/005 382/128

FOREIGN PATENT DOCUMENTS

CN 112381741 A * 2/2021 ............. G06N 3/045
WO WO-2021041125 A1 * 3/2021 ........... G06V 30/194

* cited by examiner

*Primary Examiner* — Xiao Liu
(74) *Attorney, Agent, or Firm* — Dority & Manning, PA

(57) ABSTRACT

A SPECT imaging prediction model creation method, apparatus, device, and storage medium. The method includes: obtaining a training set including a plurality of scanning image groups, wherein each scanning image group includes a standard acquisition duration SPECT image and a short acquisition duration SPECT image that corresponding to each other; performing network construction on the basis of deep convolutional neural network to obtain a network to be trained; taking the short acquisition duration SPECT image in the training set as input-side training data, taking the standard acquisition duration SPECT image in the training set as output-side training data, training the network to be trained to obtain a SPECT imaging prediction model, so as to predict SPECT prediction image of short acquisition duration SPECT image under standard acquisition duration by using the SPECT imaging prediction model. The SPECT imaging time is significantly reduced while maintaining the imaging quality of medical images.

4 Claims, 5 Drawing Sheets

(51) Int. Cl.
*A61B 6/03* (2006.01)
*G06T 12/20* (2026.01)

(52) U.S. Cl.
CPC ..... *G06T 2210/41* (2013.01); *G06T 2211/421* (2013.01); *G06T 2211/441* (2023.08)

(58) Field of Classification Search
CPC ..... G06T 11/008; A61B 6/037; A61B 6/5235; A61B 6/03; A61B 6/52; G06N 3/04; G06N 3/0455; G06N 3/0464; G06N 3/08; G06N 3/09; G06N 3/045
See application file for complete search history.

SPECT IMAGING PREDICTION MODEL CREATION METHOD AND APPARATUS, AND DEVICE AND STORAGE MEDIUM

CROSS-REFERENCE TO RELATED APPLICATION(S)

This application claims priority of the Chinese Patent Application No. 202110311613.7, titled SPECT IMAGING PREDICTION MODEL CREATION METHOD, APPARATUS, DEVICE, AND STORAGE MEDIUM, filed to China National Intellectual Property Administration on Mar. 24, 2021, the entire contents of which are incorporated herein by reference.

FIELD

The present invention relates to the technical field of SPECT, in particular to a SPECT imaging prediction model creation method, apparatus, device, and storage medium.

BACKGROUND

Single-Photon Emission Computed Tomography (SPECT) is a medical imaging technology that injects radioisotope-labeled compounds into organisms, and collects high-energy γ particles produced by decay in different directions within the same time period during biological metabolism to obtain projection signals and perform imaging by computational reconstruction. Since the signal collection depends on the half-life of the radioisotope and the number of signal collection angles, SPECT imaging faces problems such as long imaging time, and causing certain radiation damage to the human body in clinical applications. However, if reducing imaging angle or shortening imaging time, it may cause imaging results to have a series of shortcomings that damage the image quality, such as low signal-to-noise ratio, prone to artifacts, etc. Therefore, how to generate high-quality SPECT images in a short acquisition duration is an urgent problem to be solved.

SUMMARY

In view of the above, the present invention aims to provide a SPECT imaging prediction model creation method, apparatus, device, and medium, such that the SPECT imaging time can be significantly reduced while maintaining the imaging quality of medical images, improving subject comfort with SPECT imaging and reducing motion artifacts. The specific implementations are as follows.

According to a first aspect, the present invention discloses a SPECT imaging prediction model creation method, comprising:

obtaining a training set comprising a plurality of scanning image groups, wherein each scanning image group comprises a standard acquisition duration SPECT image and a short acquisition duration SPECT image that corresponding to each other;

performing network construction on the basis of deep convolutional neural network to obtain a network to be trained;

taking the short acquisition duration SPECT image in the training set as input side training data, taking the standard acquisition duration SPECT image in the training set as output side training data, and training the network to be trained to obtain a SPECT imaging prediction model, so as to predict SPECT prediction image of short acquisition duration SPECT image under standard acquisition duration by using the SPECT imaging prediction model.

Preferably, the scanning image group comprises the standard acquisition duration SPECT image, the short acquisition duration SPECT image and a CT image that corresponding to each other, wherein the CT image is used as input side training data of the network to be trained.

Preferably, the obtaining a training set comprising a plurality of scanning image groups comprises:

obtaining a standard acquisition duration γ particle signal and a short acquisition duration γ particle signal under a same acquisition condition by a single-photon emission computed tomography device;

reconstructing the standard acquisition duration γ particle signal and the short acquisition duration γ particle signal by using a reconstruction algorithm, so as to obtain corresponding standard acquisition duration SPECT image and corresponding short acquisition duration SPECT image;

obtaining the scanning image group based on the standard acquisition duration SPECT image and the short acquisition duration SPECT image.

Preferably, the obtaining a standard acquisition duration γ particle signal and a short acquisition duration γ particle signal under a same acquisition condition by a single-photon emission computed tomography device comprises:

acquiring a standard acquisition duration γ particle signal and a short acquisition duration γ particle signal under a same acquisition condition by using the single-photon emission computed tomography device according to standard acquisition duration and short acquisition duration;

or, acquiring a standard acquisition duration γ particle signal by using the single-photon emission computed tomography device according to standard acquisition duration, and then obtaining corresponding short acquisition duration γ particle signal by performing down acquisition on the standard acquisition duration γ particle signal.

Preferably, the acquisition condition comprises: starting time of acquisition, subject being acquired, radioisotope drug dosage, and acquisition angle.

Preferably, the reconstruction algorithm comprises any one of a filtered back projection, an algebraic reconstruction technique and an ordered subset conjugate gradiental.

Preferably, the performing network construction on the basis of deep convolutional neural network to obtain a network to be trained comprises:

performing network construction on the basis of U2-Net network structure to obtain the network to be trained.

According to a second aspect, the present invention discloses a SPECT imaging prediction model creation apparatus, comprising:

a training set obtaining module, configured to obtain a training set comprising a plurality of scanning image groups, wherein each scanning image group comprises a standard acquisition duration SPECT image and a short acquisition duration SPECT image that corresponding to each other;

a network construction module, configured to perform network construction on the basis of deep convolutional neural network to obtain a network to be trained;

a model training module, configured to take the short acquisition duration SPECT image in the training set as input side training data, take the standard acquisition duration SPECT image in the training set as output side training data, and train the network to be trained to obtain an SPECT imaging prediction model, so as to predict SPECT prediction image of short acquisition duration SPECT image under standard acquisition duration by using the SPECT imaging prediction model.

According to a third aspect, the present invention discloses a SPECT imaging prediction method, comprising:

obtaining a short acquisition duration SPECT image to be predicted;

inputting the short acquisition duration SPECT image to be predicted to a SPECT imaging prediction model to predict SPECT prediction image of the short acquisition duration SPECT image to be predicted under standard acquisition duration, wherein the SPECT imaging prediction model is a model obtained by training a network to be trained constructed based on deep convolutional neural network with a training set comprising a plurality of scanning image groups, wherein the scanning image group comprises a standard acquisition duration SPECT image and a short acquisition duration SPECT image that corresponding to each other.

According to a forth aspect, the present invention discloses a SPECT imaging prediction apparatus, comprising:

image obtaining module, configured to obtain a short acquisition duration SPECT image to be predicted;

image prediction module, configured to input the short acquisition duration SPECT image to be predicted to a SPECT imaging prediction model to predict SPECT prediction image of the short acquisition duration SPECT image to be predicted under standard acquisition duration, wherein the SPECT imaging prediction model is a model obtained by training a network to be trained constructed based on deep convolutional neural network with a training set comprising a plurality of scanning image groups, wherein the scanning image group comprises a standard acquisition duration SPECT image and a short acquisition duration SPECT image that corresponding to each other.

According to a fifth aspect, the present invention discloses an electronic device, comprising:

a memory, configured to store computer program;

a processor, configured to execute the computer program to implement the aforementioned SPECT imaging prediction model creation method.

According to a sixth aspect, the present invention discloses a computer-readable storage medium configured to store computer program, wherein when the computer program is executed by a processor, cause to implement the afore-mentioned SPECT imaging prediction model creation method.

In the present invention, obtaining a training set including a plurality of scanning image groups, wherein each scanning image group includes a standard acquisition duration SPECT image and a short acquisition duration SPECT image that corresponding to each other; performing network construction on the basis of deep convolutional neural network to obtain a network to be trained; taking the short acquisition duration SPECT image in the training set as input side training data, taking the standard acquisition duration SPECT image in the training set as output side training data, and training the network to be trained to obtain a SPECT imaging prediction model, so as to predict SPECT prediction image of short acquisition duration SPECT image under standard acquisition duration by using the SPECT imaging prediction model. It can be seen that, by taking the short acquisition duration SPECT image in the training set as input side training data, taking the standard acquisition duration SPECT image in the training set as output side training data, obtaining a SPECT imaging prediction model by training, then predicting SPECT prediction image of short acquisition duration SPECT image under standard acquisition duration by using the SPECT imaging prediction model, the SPECT imaging time can be significantly reduced while maintaining the imaging quality of medical images, and subject comfort with SPECT imaging can be improved and motion artifacts can be reduced.

BRIEF DESCRIPTION OF THE DRAWINGS

To describe the technical solutions in the embodiments of the present invention or the prior art more clearly, the following briefly describes the accompanying drawings needed for describing the embodiments or the prior art. Clearly, the accompanying drawings in the following description show merely embodiments of the present invention, and those of ordinary skill in the art can still derive other drawings from the provided accompanying drawings without creative efforts.

DETAILED DESCRIPTION OF EMBODIMENTS

The technical solutions in the embodiments of the present invention will be clearly and completely described below with reference to the accompanying drawings in the embodiments of the present invention. Apparently, the described embodiments are only some of the embodiments of the present invention, but not all of them. Based on the embodiments of the present invention, all other embodiments obtained by those of ordinary skill in the art without creative efforts fall within the protection scope of the present invention.

In the prior art, SPECT imaging faces problems such as long imaging time, and causing certain radiation damage to the human body in clinical applications. However, if reducing imaging angle or shortening imaging time, it may cause imaging results to have a series of shortcomings that damage the image quality, such as low signal-to-noise ratio, prone to artifacts, etc. In order to overcome the above technical problems, the present invention provides a SPECT imaging prediction model creation method.

Figure 1:
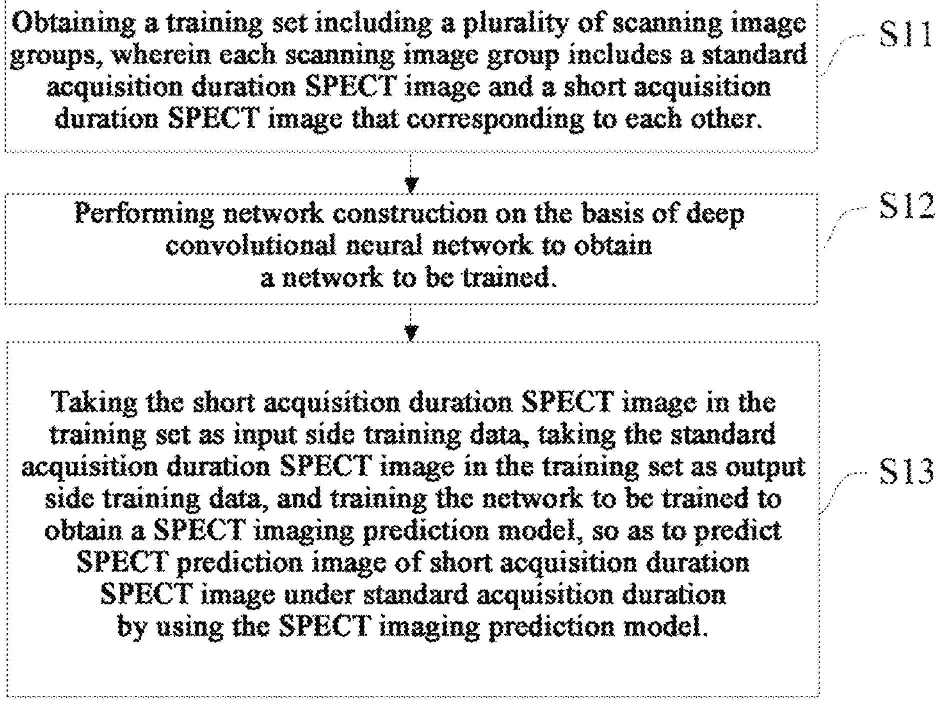
FIG. 1 is a flowchart of a SPECT imaging prediction model creation method according to the present invention.

An embodiment of the present invention discloses a SPECT imaging prediction model creation method. As shown in FIG. 1, the method may include the following steps.

Step S11: Obtaining a training set including a plurality of scanning image groups, wherein each scanning image group includes a standard acquisition duration SPECT image and a short acquisition duration SPECT image that corresponding to each other.

In the present embodiment, firstly, obtaining a plurality of scanning image groups as a training set, wherein each scanning image group includes a standard acquisition duration SPECT image and a short acquisition duration SPECT image that corresponding to each other. It can be understood that, the standard acquisition duration SPECT image and the short acquisition duration SPECT image are images acquired and reconstructed under a same acquisition condition by a single-photon emission computed tomography scanner according to the standard acquisition strategy and the fast scanning strategy. And, the SPECT image can be acquired based on a SPECT device or a SPECT+CT device.

In the present embodiment, the scanning image group may include the standard acquisition duration SPECT image, the short acquisition duration SPECT image and a CT image that corresponding to each other, where the CT image is used as input side training data of the network to be trained. It can be understood that, in addition to the standard acquisition duration SPECT image and the short acquisition duration SPECT image, the above-mentioned scanning image group may also include CT images corresponding to the above-mentioned standard acquisition duration SPECT image and short acquisition duration SPECT image. That is, the CT images are also the CT images for the same subject being acquired. In particular, the above-mentioned CT images may be acquired by a SPECT+CT device, or may be acquired by a CT device. It can be understood that, a CT image has the advantage of clear anatomical structures, and a SPECT image has the characteristic of reflecting the physiology, metabolism and function of an organ. By building a training set including standard acquisition duration SPECT images, short acquisition duration SPECT images, and CT images, the subsequent training may utilize the characteristics of various images to improve the training effect.

Step S12: Performing network construction on the basis of deep convolutional neural network to obtain a network to be trained.

In the present embodiment, performing network construction on the basis of deep convolutional neural network to obtain the network to be trained. In particular, build sub-encoders and sub-decoders based on convolutional layer, BN (Batch Normalization) layer and Relu layer. Then, connect different preset numbers of sub-encoders and sub-decoders in sequence via pooling layer or sampling layer to build encoders and decoders of different sizes. Finally, by connecting the encoders and decoders of different sizes in series, obtain the network to be trained. In particular, the above-mentioned deep convolutional neural network may be an image reconstruction convolutional network composed of N convolutional neural network (CNN) units connected in series and including a symmetrical serially connected encoder-decoder structure, in which each convolutional neural network unit consists of a preset number of convolutional layer, pooling layer, nonlinear layer, skip connection layer, and the corresponding down-sampling and up-sampling layers.

Figure 2:
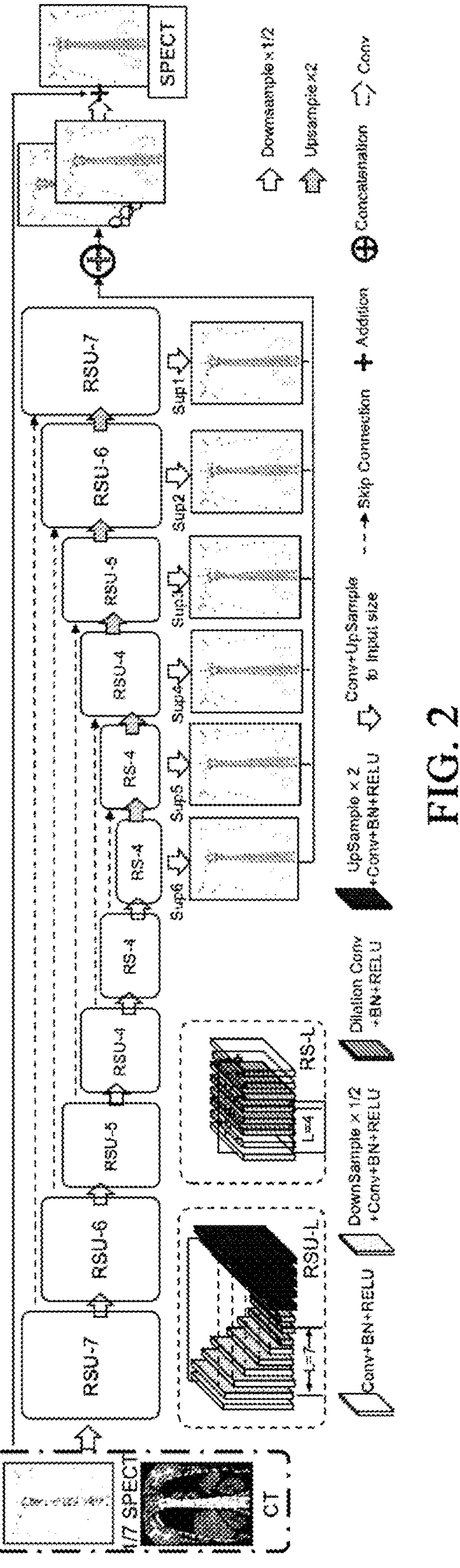
FIG. 2 is a structural schematic diagram of a SPECT imaging prediction model according to the present invention.

In the present embodiment, perform network construction on the basis of deep convolutional neural network to obtain the network to be trained may include: performing network construction on the basis of U2-Net network structure to obtain the network to be trained. It can be understood that, on the basis of U2-Net network structure, construct a network to be trained including a plurality of serially connected encoders and decoders. In particular, the structural schematic diagram of the above-mentioned network to be trained is shown as FIG. 2. Each level of the encoder and decoder structure consists of RSU units (residual U-block). Each RSU consists of 3-5 levels of serially connected sub-encoder and sub-decoder. The sub-encoder and sub-decoder consist of several 3×3 convolutional layers, BN layers, and Relu nonlinear layers. The sub-encoder and sub-decoder are connected by 2×2 pooling layer or up-sampling layer. And, different sizes of receptive fields are mixed by the Dilation Conv included in RSU. Therefore, regardless of the resolution, the model can capture local and global information from shallow layer and deep layer. The depth of the entire network is also increased without significantly increasing the amount of calculation. At the same time, Skip Connection is used to introduce the feature information on the corresponding scale into the up-sampling process, solving the problems of gradient explosion and gradient disappearance in the training process in the deep network.

Step S13: Taking the short acquisition duration SPECT image in the training set as input side training data, taking the standard acquisition duration SPECT image in the training set as output side training data, and training the network to be trained to obtain a SPECT imaging prediction model, so as to predict SPECT prediction image of short acquisition duration SPECT image under standard acquisition duration by using the SPECT imaging prediction model.

In the present embodiment, after obtaining the training set and constructing the network to be trained, take the short acquisition duration SPECT image in the above-mentioned training set as input side training data, take the standard acquisition duration SPECT image in the above-mentioned training set as output side training data, and train the above-mentioned constructed network to be trained to obtain a SPECT imaging prediction model, so as to predict SPECT prediction image of short acquisition duration SPECT image under standard acquisition duration by using the SPECT imaging prediction model. Among them, the above-mentioned training set may be divided into training data and testing data. Train the model using the training data and then test the performance of the model using the testing data to obtain a SPECT imaging prediction model that meets the prediction standards.

As can be seen from the above, in the present embodiment, obtaining a training set including a plurality of scanning image groups, wherein each scanning image group includes a standard acquisition duration SPECT image and a short acquisition duration SPECT image that corresponding to each other; performing network construction on the basis of deep convolutional neural network to obtain a network to be trained; taking the short acquisition duration SPECT image in the training set as input side training data, taking the standard acquisition duration SPECT image in the training set as output side training data, and training the network to be trained to obtain a SPECT imaging prediction model, so as to predict SPECT prediction image of short acquisition duration SPECT image under standard acquisition duration by using the SPECT imaging prediction model. It can be seen that, by taking the short acquisition duration SPECT image in the training set as input side training data, and taking the standard acquisition duration SPECT image in the training set as output side training data, obtaining a SPECT imaging prediction model by training, then predicting SPECT prediction image of short acquisition duration SPECT image under standard acquisition duration by using the SPECT imaging prediction model, the SPECT imaging time can be significantly reduced while maintaining the imaging quality of medical images, and subject comfort with SPECT imaging can be improved and motion artifacts can be reduced.

Figure 3:
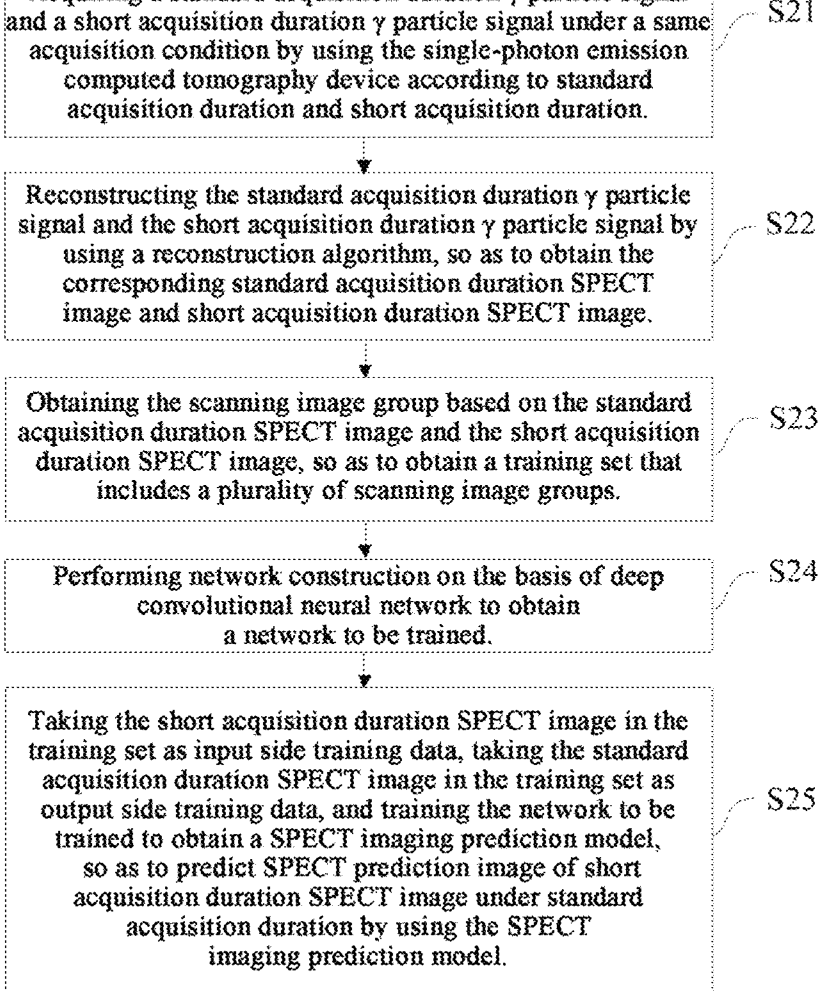
FIG. 3 is a specific flowchart of a SPECT imaging prediction model creation method according to the present invention.

An embodiment of the present invention discloses a specific SPECT imaging prediction model creation method. As shown in FIG. 3, the method may include the following steps.

Step S21: Acquiring a standard acquisition duration γ particle signal and a short acquisition duration γ particle signal under a same acquisition condition by using the single-photon emission computed tomography device according to standard acquisition duration and short acquisition duration.

In the present embodiment, using the single-photon emission computed tomography device may be specifically using the SPECT/CT scanner according to standard acquisition duration and short acquisition duration, to acquire a standard acquisition duration γ particle signal and a short acquisition duration γ particle signal under a same acquisition condition. In the present embodiment, the acquisition condition may include starting time of acquisition, subject being acquired, radioisotope drug dosage, and acquisition angle. It can be understood that, use the single-photon emission computed tomography device to collect more than 10 groups of standard acquisition duration γ particle signal and short acquisition duration γ particle signal under the same acquisition condition, (that is, injecting the same isotope-labeled compound of the same dose into one patient at a time), and acquire projection signal groups with the same number of angles, then two signals with different numbers of γ particles acquired at the same projection angle are obtained.

Among those, the above-mentioned short acquisition duration γ particle signal may be 1/7 of the standard acquisition duration. For example, use SPECT/CT scanner Siemens-Symbia-Intevo to acquire whole-body quantitative bone imaging of 20 subjects. Wherein, the injection dose can be 25-30 mci. Two scanning protocols are set up for the subjects: one is standard scanning, that is, 20 seconds per frame, and then obtain the γ particle signals of the standard acquisition duration; and the other is fast scanning, that is, 3 seconds per frame, and then obtain the γ particle signals of 1/7 acquisition duration. Other sampling parameters are: 60 frames, single probe rotation of 180°, single rotation of 6°. Use the Ordered Subset Conjugate Gradient (OSCG) algorithm to reconstruct the SPECT projection data, in order to obtain the standard acquisition duration SPECT image and the short acquisition duration SPECT image that corresponding to each other. It should be noted that, the scope of acquisition of the present embodiment includes but is not limited to brain, bone, heart and other parts.

In the present embodiment, it may also use the single-photon emission computed tomography device to acquire standard acquisition duration γ particle signals according to standard acquisition duration, then perform down acquisition on the standard acquisition duration γ particle signals to obtain the corresponding short acquisition duration γ particle signals. It can be understood that, the short acquisition duration γ particle signals can either be obtained by acquiring, or be obtained by performing down acquisition on the standard acquisition duration γ particle signals.

Step S22: Reconstructing the standard acquisition duration γ particle signal and the short acquisition duration γ particle signal by using a reconstruction algorithm, so as to obtain corresponding standard acquisition duration SPECT image and corresponding short acquisition duration SPECT image.

In the present embodiment, using the reconstruction algorithm to reconstruct the acquired standard acquisition duration γ particle signals and short acquisition duration γ particle signals, and obtaining corresponding standard acquisition duration SPECT image and corresponding short acquisition duration SPECT image. In the present embodiment, the reconstruction algorithm includes but is not limited to filter back projection (FBP), algebraic reconstruction technique (ART) and ordered subset conjugate gradiental (OSCG).

Step S23: Obtaining the scanning image group based on the standard acquisition duration SPECT image and the short acquisition duration SPECT image, so as to obtain a training set that includes a plurality of scanning image groups.

In the present embodiment, according to the obtained standard acquisition duration SPECT image and short acquisition duration SPECT image as mentioned above, the scanning image group is obtained, so as to obtain the training set that includes a plurality of scanning image groups.

Step S24: Performing network construction on the basis of deep convolutional neural network to obtain a network to be trained.

Step S25: Taking the short acquisition duration SPECT image in the training set as input side training data, taking the standard acquisition duration SPECT image in the training set as output side training data, and training the network to be trained to obtain a SPECT imaging prediction model, so as to predict SPECT prediction image of short acquisition duration SPECT image under standard acquisition duration by using the SPECT imaging prediction model.

Figure 4:
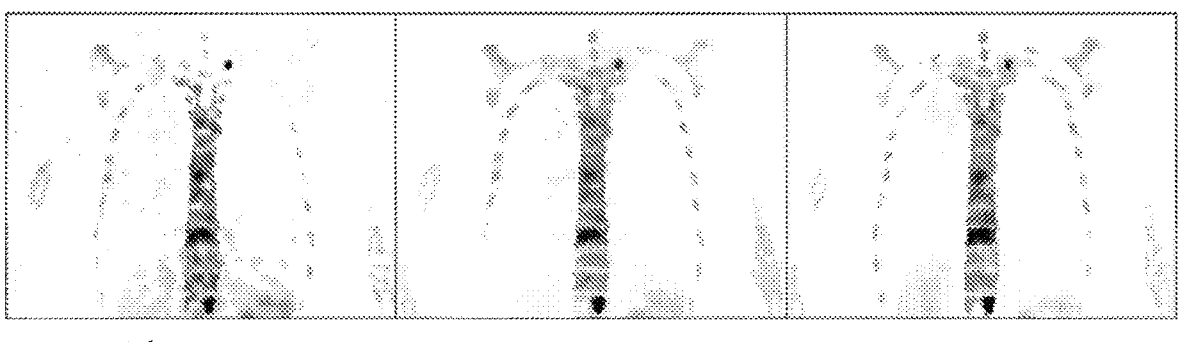
FIG. 4 is a schematic diagram of SPECT imaging according to the present invention.

In the present embodiment, predict the SPECT prediction image of a 1/7 SPECT image under the standard acquisition duration with the trained SPECT imaging prediction model based on the input 1/7 SPECT image. After the SPECT imaging prediction model is trained, the model may be qualitatively and quantitatively evaluated by using Structural SIMilarity (SSIM) and Peak Signal to Noise Ratio (PSNR, Peak Signal to Noise Ratio) indicators to detect the model effect. Take the 1/7 SPECT image, and the SPECT prediction image reconstructed by deep learning, and the SPECT image under standard acquisition shown in FIG. 4 as an example. In can be seen that the quality of the predicted SPECT image is equivalent to that of the standard SPECT image, and is much better than the original 1/7 SPECT image. It is relatively difficult to identify the lesion area on the 1/7 SPECT image, while it is much easier to identify the lesion area on the predicted SPECT image.

Among them, the specific process of the above-mentioned step S24 and step S25 may refer to the corresponding content disclosed in the foregoing embodiments. No further details are given here.

As can be seen from the above, acquire a standard acquisition duration γ particle signal and a short acquisition duration γ particle signal under a same acquisition condition by using the single-photon emission computed tomography device according to standard acquisition duration and short acquisition duration; then reconstruct the standard acquisition duration γ particle signal and the short acquisition duration γ particle signal by using a reconstruction algorithm, so as to obtain corresponding standard acquisition duration SPECT image and corresponding short acquisition duration SPECT image; and finally obtain the scanning image group based on the standard acquisition duration SPECT image and the short acquisition duration SPECT image, so as to obtain a training set that includes a plurality of scanning image groups. As a result, take the short acquisition duration SPECT image in the training set as input side training data, take the standard acquisition duration SPECT image in the training set as output side training data, and train the network to be trained to obtain the SPECT imaging prediction model, which can predict the corresponding standard acquisition duration SPECT image based on the short acquisition duration SPECT image. In comparison with traditional SPECT imaging methods, in the present embodiment, the imaging time can be significantly reduced while maintaining the imaging quality of images, and subject comfort with SPECT imaging can be improved, the signal-to-noise ratio can be improved and motion artifacts can be reduced.

Figure 5:
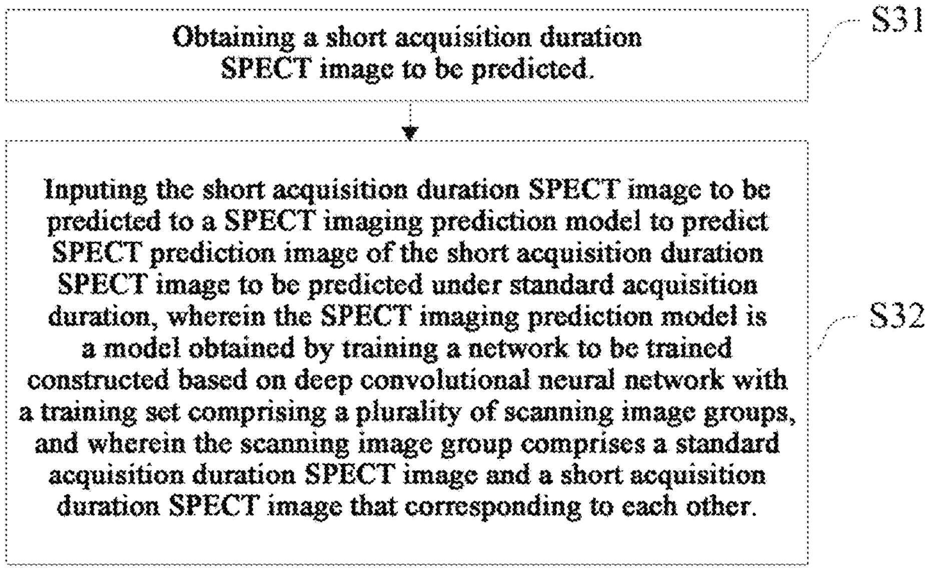
FIG. 5 is a flowchart of a SPECT imaging prediction method according to the present invention.

An embodiment of the present invention discloses a SPECT imaging prediction method. As shown in FIG. 5, the method may include the following steps.

Step S31: Obtaining a short acquisition duration SPECT image to be predicted.

In the present embodiment, firstly, obtaining a short acquisition duration SPECT image to be predicted.

Step S32: Inputting the short acquisition duration SPECT image to be predicted to a SPECT imaging prediction model to predict SPECT prediction image of the short acquisition duration SPECT image to be predicted under standard acquisition duration, wherein the SPECT imaging prediction model is a model obtained by training a network to be trained constructed based on deep convolutional neural network with a training set comprising a plurality of scanning image groups, and wherein the scanning image group comprises a standard acquisition duration SPECT image and a short acquisition duration SPECT image that corresponding to each other.

In the present embodiment, inputting the acquired short acquisition duration SPECT image into the SPECT imaging prediction model to predict SPECT prediction image of the above-mentioned short acquisition duration SPECT image to be predicted under standard acquisition duration. Among which, the above-mentioned SPECT imaging prediction model is a model obtained by training a network to be trained constructed based on deep convolutional neural network with a training set comprising a plurality of scanning image groups. Among which, the above-mentioned scanning image group comprises a standard acquisition duration SPECT image and a short acquisition duration SPECT image that corresponding to each other.

In the present embodiment, the process of obtaining a training set including a plurality of scanning image groups includes: obtaining a standard acquisition duration γ particle signal and a short acquisition duration γ particle signal under a same acquisition condition by a single-photon emission computed tomography device; reconstructing the standard acquisition duration γ particle signal and the short acquisition duration γ particle signal by using a reconstruction algorithm, so as to obtain corresponding standard acquisition duration SPECT image and corresponding short acquisition duration SPECT image; and obtaining the scanning image group based on the standard acquisition duration SPECT image and the short acquisition duration SPECT image. Among them, the above-mentioned obtaining a standard acquisition duration γ particle signal and a short acquisition duration γ particle signal under a same acquisition condition by a single-photon emission computed tomography device may include: acquiring a standard acquisition duration γ particle signal and a short acquisition duration γ particle signal under a same acquisition condition by using the single-photon emission computed tomography device according to standard acquisition duration and short acquisition duration; or acquiring a standard acquisition duration γ particle signal by using the single-photon emission computed tomography device according to standard acquisition duration, and then obtaining corresponding short acquisition duration γ particle signal by performing down acquisition on the standard acquisition duration γ particle signal. Among them, the abovementioned acquisition condition includes: starting time of acquisition, subject being acquired, radioisotope drug dosage, and acquisition angle. Among them, the above-mentioned reconstruction algorithm includes but is not limited to filter back projection, algebraic reconstruction technique and ordered subset conjugate gradiental. In the present embodiment, the above-mentioned network to be trained may the network to be trained obtained by performing network construction on the basis of U2-Net network structure.

As can be seen from the above, in the present embodiment, use the SPECT imaging prediction model to predict the acquired short acquisition duration SPECT image, and obtain the SPECT prediction image under standard acquisition duration, which corresponds to the short acquisition duration SPECT image. In this way, the SPECT imaging time can be significantly reduced while maintaining the imaging quality of medical images, and also improve subject comfort with SPECT imaging and reduce motion artifacts.

Figure 6:
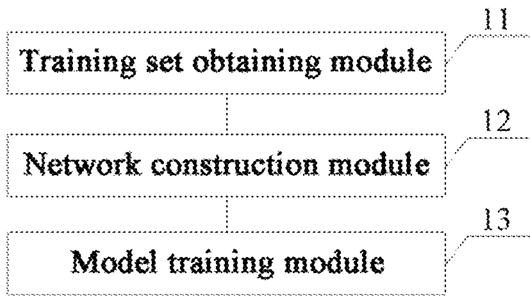
FIG. 6 is a structural schematic diagram of a SPECT imaging prediction model creation apparatus according to the present invention.

Accordingly, an embodiment of the present invention also discloses a SPECT imaging prediction model creation apparatus. As shown in FIG. 6, the apparatus includes:

A training set obtaining module 11, which is configured to obtain a training set including a plurality of scanning image groups. Among which, each scanning image group includes a standard acquisition duration SPECT image and a short acquisition duration SPECT image that corresponding to each other.

A network construction module 12, which is configured to perform network construction on the basis of deep convolutional neural network to obtain a network to be trained.

A model training module 13, which is configured to: take the short acquisition duration SPECT image in the training set as input side training data, take the standard acquisition duration SPECT image in the training set as output side training data, and train the network to be trained to obtain an SPECT imaging prediction model, so as to predict SPECT prediction image of short acquisition duration SPECT image under standard acquisition duration by using the SPECT imaging prediction model.

As can be seen from the above, in the present embodiment, obtaining a training set including a plurality of scanning image groups, wherein each scanning image group includes a standard acquisition duration SPECT image and a short acquisition duration SPECT image that corresponding to each other; performing network construction on the basis of deep convolutional neural network to obtain a network to be trained; taking the short acquisition duration SPECT image in the training set as input side training data, taking the standard acquisition duration SPECT image in the training set as output side training data, and training the network to be trained to obtain a SPECT imaging prediction model, so as to predict SPECT prediction image of short acquisition duration SPECT image under standard acquisition duration by using the SPECT imaging prediction model. It can be seen that, by taking the short acquisition duration SPECT image in the training set as input side training data, and taking the standard acquisition duration SPECT image in the training set as output side training data, obtaining a SPECT imaging prediction model by training, then predicting SPECT prediction image of short acquisition duration SPECT image under standard acquisition duration by using the SPECT imaging prediction model, the SPECT imaging time can be significantly reduced while maintaining the imaging quality of medical images, and subject comfort with SPECT imaging can be improved and motion artifacts can be reduced.

In some specific embodiments, the scanning image group includes the standard acquisition duration SPECT image, the short acquisition duration SPECT image, and a CT image that corresponding to each other, where the CT image is used as input side training data of the network to be trained.

In some specific embodiments, the training set obtaining module 11 may particularly include:

A γ particle signal acquisition unit, which is configured to obtain a standard acquisition duration γ particle signal and a short acquisition duration γ particle signal under a same acquisition condition by a single-photon emission computed tomography device.

An image reconstruction unit, which is configured to reconstruct the standard acquisition duration γ particle signal and the short acquisition duration γ particle signal by using a reconstruction algorithm, so as to obtain corresponding standard acquisition duration SPECT image and corresponding short acquisition duration SPECT image.

A scanning image group determination unit, which is configured to obtain the scanning image group based on the standard acquisition duration SPECT image and the short acquisition duration SPECT image.

In some specific embodiments, the γ particle signal acquisition unit may particularly include:

A first acquisition unit, which is configured to acquire a standard acquisition duration γ particle signal and a short acquisition duration γ particle signal under a same acquisition condition by using the single-photon emission computed tomography device according to standard acquisition duration and short acquisition duration.

A second acquisition unit, which is configured to acquire a standard acquisition duration γ particle signal by using the single-photon emission computed tomography device according to standard acquisition duration, and then obtaining corresponding short acquisition duration γ particle signal by performing down acquisition on the standard acquisition duration γ particle signal.

In some specific embodiments, the acquisition condition may particularly include starting time of acquisition, subject being acquired, radioisotope drug dosage, and acquisition angle.

In some specific embodiments, the reconstruction algorithm may particularly include any one of a filter back projection, an algebraic reconstruction technique and an ordered subset conjugate gradiental.

In some specific embodiments, the network construction module 12 may particularly include:

A network construction unit, which is configured to perform network construction on the basis of U2-Net network structure to obtain the network to be trained.

Figure 7:
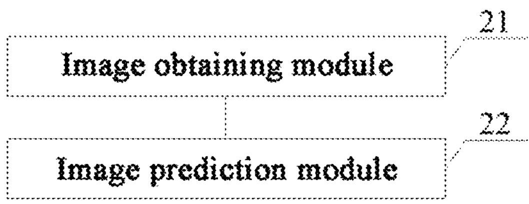
FIG. 7 is a structural schematic diagram of a SPECT imaging prediction apparatus according to the present invention.

Accordingly, an embodiment of the present invention also discloses a SPECT imaging prediction apparatus. As shown in FIG. 7, the apparatus includes:

An image obtaining module 21, which is configured to obtain a short acquisition duration SPECT image to be predicted.

An image prediction module 22, which is configured to input the short acquisition duration SPECT image to be predicted to a SPECT imaging prediction model to predict SPECT prediction image of the short acquisition duration SPECT image to be predicted under standard acquisition duration, wherein the SPECT imaging prediction model is a model obtained by training a network to be trained constructed based on deep convolutional neural network with a training set comprising a plurality of scanning image groups, wherein the scanning image group comprises a standard acquisition duration SPECT image and a short acquisition duration SPECT image that corresponding to each other.

As can be seen from the above, in the present embodiment, use the SPECT imaging prediction model to predict the acquired short acquisition duration SPECT image, and obtain the SPECT prediction image under standard acquisition duration, which corresponds to the short acquisition duration SPECT image. In this way, the SPECT imaging time can be significantly reduced while maintaining the imaging quality of medical images, and subject comfort with SPECT imaging can be improved and motion artifacts can be reduced.

Figure 8:
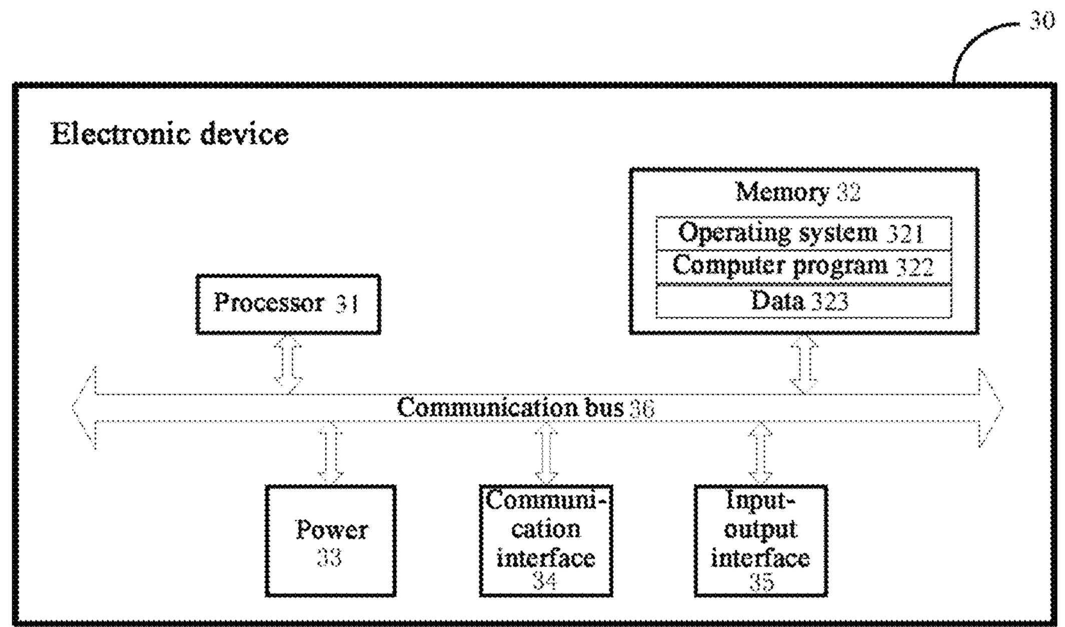
FIG. 8 is a structural diagram of an electronic device according to the present invention.

Further, an embodiment of the present invention also discloses an electronic device, as shown in FIG. 8. The content in the figure should not be considered as any limitation on the scope of the present invention.

FIG. 8 is a structural diagram illustrating an electronic device 30 according to the embodiments of the present invention. The electronic device 30 may particularly include: at least one processor 31, at least one memory 32, a power 33, a communication interface 34, an input-output (I/O) interface 35, and a communication bus 36. Among them, the memory 32 is configured to store computer program. The computer program is loaded and executed by the processor 31 to implement relevant steps in the SPECT imaging prediction model creation method disclosed in any of the afore-mentioned embodiments.

In the present embodiment, the power 33 is configured to provide working voltage for each hardware device on the electronic device 30. The communication interface 34 is configured to provide a data transmission channel between the electronic device 30 and external devices. The communication protocol to be followed may be any communication protocol suitable for the technical solution of the present invention, which is not specifically limited here. The input-output (I/O) interface 35 is configured to receive input data from the outside or output data to the outside. The type of the interface can be determined according to the needs of specific applications, and is not specifically limited here.

In addition, the memory 32, as a carrier for resource storage, can be a read-only memory, a random access memory, a disk or a disc, etc. The resources stored thereon include: operating system 321, computer program 322, and data 323 which includes scanned image groups, etc. The manner of storage can be either temporary storage or permanent storage.

Among them, the operating system 321 is configured to manage and control each hardware device and the computer program 322 on the electronic device 30 to cause the processor 31 to calculate and process the massive data 323 in the memory 32. It can be Windows Server, Netware, Unix, Linux, etc. In addition to computer programs that can be used to complete the SPECT imaging prediction model creation method executed by the electronic device 30 disclosed in any of the afore-mentioned embodiments, the computer program 322 may further include computer programs that can be used to complete other specific tasks.

Furthermore, embodiments of the present application also disclose a computer storage medium. The computer storage medium has computer-executable instructions stored thereon. When the computer-executable instructions are loaded and executed by the processor, it implements the steps of the SPECT imaging prediction model creation method disclosed in any of the afore-mentioned embodiments.

Each embodiment in this specification is described in a progressive manner. Each embodiment focuses on the differences from other embodiments. The same or similar parts between the various embodiments can be referred to each other. As for the apparatuses disclosed in the embodiments, since they correspond to the methods disclosed in the embodiments, the description is relatively simple. Relevant details may refer to the description of the methods.

The steps of the methods or algorithms described in connection with the embodiments disclosed herein may be directly implemented by hardware, software modules executed by the processor, or the combination thereof. Software modules can be placed in random access memory (RAM), memory, read-only memory (ROM), electrically programmable ROM, electrically erasable programmable ROM, registers, hard disk, removable disk, CD-ROM, or any other form of storage medium known in the technical field.

Finally, it should also be noted that, relational terms herein, such as first and second, are used only to distinguish one entity or operation from another, and do not necessarily require or imply such actual relationship or ordering of these entities or operations. Furthermore, the term 'comprise', 'include' or any other variation thereof is intended to cover a non-exclusive inclusion. Thus, a process, method, article, or device that includes a set of elements includes not only those elements, but also includes other elements not expressly listed, or elements that are inherent to the process, method, article or device. Without further limitation, an element defined by the phrase "comprising/including . . . " does not exclude the presence of additional identical elements in the process, method, article or apparatus that includes the stated element.

The SPECT imaging prediction model creation method, apparatus, device, and medium provided by the present invention are described in detail above. Herein, specific examples are used to illustrate the principles and implementations of the present invention. The description of the above embodiments is only for understanding the method and core idea of the present invention. Meanwhile, for those of ordinary skill in the art, there will be changes in specific implementations and the scope of applications according to the concept of the present invention. In summary, the contents of the specification should not be construed as limiting the present invention.

What is claimed is:

1. A single-photon emission computed tomography (SPECT) imaging prediction model creation method, comprising:

obtaining a training set comprising a plurality of scanning image groups, wherein each of the scanning image groups comprises a standard acquisition duration SPECT image and a short acquisition duration SPECT image, and a computed tomography (CT) image corresponding to a same subject being acquired;

wherein the obtaining a training set comprising a plurality of scanning image groups comprises:

acquiring, by a single-photon emission computed tomography device, a standard acquisition duration γ particle signal according to a standard acquisition duration;

obtaining a corresponding short acquisition duration γ particle signal by performing down acquisition on the standard acquisition duration γ particle signal, the standard acquisition duration γ particle signal and the short acquisition duration γ particle signal being under a same acquisition condition including a starting time of acquisition, the subject being acquired, a radioisotope drug dosage, and an acquisition angle; and reconstructing the standard acquisition duration γ particle signal and the short acquisition duration γ particle signal by using a reconstruction algorithm, so as to obtain the standard acquisition duration SPECT image and the short acquisition duration SPECT image;

performing network construction on the basis of a U2-Net network structure to obtain a network to be trained, wherein the network to be trained comprises a plurality of serially connected encoders and decoders, each level of the encoders and decoders consisting of a residual U-block (RSU), each RSU comprising 3-5 levels of serially connected sub-encoders and sub-decoders, the sub-encoders and sub-decoders comprising 3×3 convolutional layers, batch normalization layers, and rectified linear unit nonlinear layers connected by 2×2 pooling layers or up-sampling layers, with dilation convolution mixing receptive fields and skip connections introducing feature information at corresponding scales into an up-sampling process; and taking the short acquisition duration SPECT image and the CT image as input-side training data, taking the standard acquisition duration SPECT image as output-side training data, and training the network to be trained to obtain a SPECT imaging prediction model.

2. The SPECT imaging prediction model creation method according to claim 1, wherein the reconstruction algorithm comprises any one of a filtered back projection, an algebraic reconstruction technique and an ordered subset conjugate gradiental.

3. An electronic device, comprising:

a memory, configured to store a computer program;

a processor, configured to execute the computer program to cause the electronic device to:

obtain a training set comprising a plurality of scanning image groups, wherein each of the scanning image groups comprises a standard acquisition duration single-photon emission computed tomography (SPECT) image and a short acquisition duration SPECT image, and a-computed tomography (CT) image corresponding to a same subject being acquired;

acquire, by a single-photon emission computed tomography device, a standard acquisition duration γ particle signal according to a standard acquisition duration;

obtain a corresponding short acquisition duration γ particle signal by performing down acquisition on the standard acquisition duration γ particle signal, the standard acquisition duration γ particle signal and the short acquisition duration γ particle signal being under a same acquisition condition including a starting time of acquisition, the subject being acquired, a radioisotope drug dosage, and an acquisition angle;

reconstruct the standard acquisition duration γ particle signal and the short acquisition duration γ particle signal by using a reconstruction algorithm, so as to obtain the standard acquisition duration SPECT image and the short acquisition duration SPECT image;

perform network construction on the basis of a U2-Net network structure to obtain a network to be trained, wherein the network to be trained comprises a plurality of serially connected encoders and decoders, each level of the encoders and decoders consisting of a residual U-block (RSU), each RSU comprising 3-5 levels of serially connected sub-encoders and sub-decoders, the sub-encoders and sub-decoders comprising 3×3 convolutional layers, batch normalization layers, and rectified linear unit nonlinear layers connected by 2×2 pooling layers or up-sampling layers, with dilation convolution mixing receptive fields and skip connections introducing feature information at corresponding scales into an up-sampling process; and take the short acquisition duration SPECT image and the CT image in the training set as input-side training data, take the standard acquisition duration SPECT image in the training set as output-side training data, and train the network to be trained to obtain a SPECT imaging prediction model.

4. A non-transitory computer-readable storage medium, configured to store a computer program, wherein when the computer program is executed by a processor of an electronic device, the electronic device is caused to:

obtain a training set comprising a plurality of scanning image groups, wherein each of the scanning image groups comprises a standard acquisition duration single-photon emission computed tomography (SPECT) image and a short acquisition duration SPECT image, and a computed tomography (CT) image corresponding to a same subject being acquired;

acquire, by a single-photon emission computed tomography device, a standard acquisition duration γ particle signal according to a standard acquisition duration;

obtain a corresponding short acquisition duration γ particle signal by performing down acquisition on the standard acquisition duration γ particle signal, the standard acquisition duration γ particle signal and the short acquisition duration γ particle signal being under a same acquisition condition including a starting time of acquisition, the subject being acquired, a radioisotope drug dosage, and an acquisition angle;

reconstruct the standard acquisition duration γ particle signal and the short acquisition duration γ particle signal by using a reconstruction algorithm, so as to obtain the standard acquisition duration SPECT image and the short acquisition duration SPECT image;

perform network construction on the basis of a U2-Net network structure to obtain a network to be trained, wherein the network to be trained comprises a plurality of serially connected encoders and decoders, each level of the encoders and decoders consisting of a residual U-block (RSU), each RSU comprising 3-5 levels of serially connected sub-encoders and sub-decoders, the sub-encoders and sub-decoders comprising 3×3 convolutional layers, batch normalization layers, and rectified linear unit nonlinear layers connected by 2×2 pooling layers or up-sampling layers, with dilation convolution mixing receptive fields and skip connections introducing feature information at corresponding scales into an up-sampling process; and take the short acquisition duration SPECT image and the CT image in the training set as input-side training data, take the standard acquisition duration SPECT image in the training set as output-side training data, and train the network to be trained to obtain a SPECT imaging prediction model.

* * * * *